Figure 1:
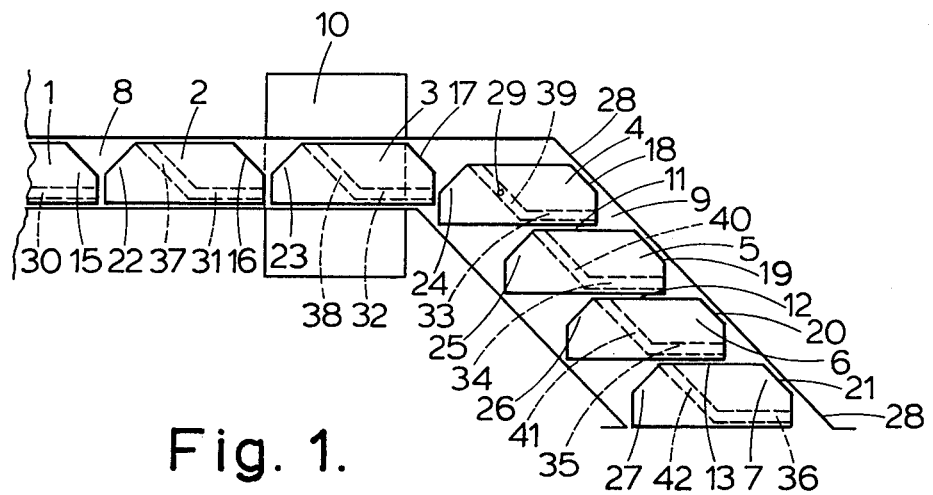

United States Patent [19]

Brook et al.

[11] 4,191,287

[45] Mar. 4, 1980

[54] AUTOMATIC TRANSPORT MECHANISM AND A CARRIER MEMBER FOR USE THEREWITH

[75] Inventors: Neil R. Brook, Cambridge; Peter J. Maling, Little Eversden, both of England

[73] Assignee: PYE (Electronic Products) Limited, Cambridge, England

[21] Appl. No.: 951,229

[22] Filed: Oct. 13, 1978

[30] Foreign Application Priority Data

Oct. 18, 1977 [GB] United Kingdom ............... 43302/77

[51] Int. Cl.² ............................................. B65G 35/06
[52] U.S. Cl. ..................................... 198/472; 198/795
[58] Field of Search ............... 198/472, 580, 648, 795, 198/798; 141/130; 422/70

[56] References Cited

U.S. PATENT DOCUMENTS 3,418,084  12/1968  Allington ........................ 198/472 X
4,040,533  8/1977  DeBoer et al. .................. 198/472 X
4,147,250  4/1979  Schulz ............................ 198/472

*Primary Examiner*—Jeffrey V. Nase
*Attorney, Agent, or Firm*—Thomas A. Briody; Jack Oisher; Paul R. Miller

[57] ABSTRACT

A transport mechanism for transporting a series of carrier members carrying a plurality of receptacles through a processing zone wherein the carrier members are sequentially driven in a first passageway and are passed to a second and optionally to a third passageway by (a) angled guide grooves in the base of each member and pivots in the floor of the passageway and (b) angled camming surfaces respectively at the leading edge of each carrier member and at an appropriate corner between the first passageway and the second passageway. Each carrier member may contain materials in the receptacles for sampling, analysing or for automatic laboratory testing in the processing zone.

11 Claims, 7 Drawing Figures

AUTOMATIC TRANSPORT MECHANISM AND A CARRIER MEMBER FOR USE THEREWITH

This invention relates to an automatic transport mechanism and to a carrier member for use therewith, the automatic transport mechanism being of the kind which transports a series of carrier members through a processing zone comprising a first passageway along the floor of which substantially reactangular carrier members pass in end to end contact via the processing zone, to a second, outlet passageway continuous with the first passageway, said second, outlet passageway being orientated in the same plane at an angle of less than 90° to the first passageway in the direction of passage of the carrier members and having an inner and an outer wall spaced apart with a width which is wider than the first passageway by an amount which is sufficient to allow each carrier member to proceed in side to side contact with adjacent members, primary driving means for driving each carrier member in turn along at least a part of the first passageway, means for redirecting each carrier member in turn on passing from the first passageway to the second, outlet passageway comprising at least one oblique wall surface which forms a tapered section substantially at the leading end of each carrier member for slidably engaging, when in operation, an oblique wall surface formed by at least an initial part of the outer wall of the second, outlet, passageway.

It is known to use chemical fraction collectors for collecting liquid samples from chromatographic apparatus for the purpose of analysis. U.K. Patent Specification No. 1,192,388 describes an apparatus for collecting chemical fractions which includes two spaced parallel chambers adjacent ends of said chambers being interconnected by parallel transfer passageways, a plurality of shuttles, each being arranged to carry a plurality of fraction containers and having camming surfaces formed at its ends, a shuttle being disposed in each of the transfer passageways, the remaining shuttles being disposed in rows in the chambers so as to lie substantially parallel to the shuttles in the passageway and means including drive means for moving the shuttles successively through a filling station located in one of the passageways, the drive means moving the shuttle in one of the passageways into end engagement with a further shuttle in one of the chambers, the camming surfaces co-operating to displace the further shuttle laterally with respect to the direction of movement of said shuttle from said one passageway, the drive means also moving the shuttle in the other passageway simultaneously in the opposite direction through the other passageway, to displace a further shuttle in the other chamber laterally, the lateral movement of each of the further shuttles causing a foremost shuttle at the other end of the respective chamber to be moved into alignment with the respective passageway. The apparatus of Specification No. 1,192,388 has the disadvantage that there are required two spaced parallel chambers adjacent ends of which are interconnected by parallel transfer passageways. A plurality of shuttles with at least one shuttle in each transfer passageway is also required whilst the remaining shuttles are in the chambers. Parallel movements of the shuttles in opposite directions can therefore only occur. A further disadvantage is that the drive means itself has to move each shuttle from one chamber to the other chamber. The shuttles are each tapered to a point at each end to form camming surfaces. The camming surfaces are furthermore recessed to form an upstanding hook member at a left hand end of each shuttle with a similar construction but reversely disposed at the right hand end. Tilting of the shuttles as they pass out of the transfer passageways into the magazines is avoided in one example only by having an additional four inner corners of the chamber with oblique surfaces. However, the hook members still slidably engage each other at one end as the shuttles pass out of the transfer passageways whilst the other end engages the oblique corner surface of the chamber. This construction is both expensive to produce and is limited in its application.

One object of the present invention is to provide an automatic transport mechanism which is of a simple construction and which mitigates the aforesaid disadvantages.

A further object of the invention to provide an automatic transport mechanism which is not restricted to a closed circuit for the carrier members. Furthermore, the individual carrier members of the present invention do not need to be hooked or linked together and are not subject to tilting on changing direction. The right hand and left hand ends of each carrier member may be designed so that they are either both different or identical in construction. This also allows the end or ends of each carrier member to be used for alternative functions.

According to the present invention there is provided an automatic transport mechanism for transporting a series of carrier members through a processing zone comprising a first passageway along the floor of which substantially rectangular carrier members pass in end to end contact via the processing zone, to a second, outlet, passageway continuous with the first passageway, said second, outlet, passageway being orientated in the same plane at an angle of less than 90° to the first passageway in the direction of passage of the carrier members and having an inner and an outer wall spaced apart with a width which is wider than the first passageway by an amount which is sufficient to allow each carrier member to proceed in side to side contact with adjacent members, primary driving means for driving each carrier member in turn along at least a part of the first passageway, means for redirecting each carrier member in turn on passing from the first passageway to the second, outlet, passageway comprising at least one oblique wall surface which forms a tapered section substantially at the leading end of each carrier member for slidably engaging, when in operation, an oblique wall surface formed by at least an initial part of the outer wall of the second, outlet, passageway and characterised in that the floor of the first passageway has at least one pivot which can freely project into an open-ended inlet groove along the base of the carrier member and can be allowed to pass along the groove parallel with the longitudinal axis of the carrier member, after which passage, the or each pivot enters, into slidable engagement with a corresponding number of open-ended outlet grooves continuous with the inlet groove but each orientated at the same angle to the inlet groove as the second, outlet, passageway is orientated to the first passageway, the or each pivot being spaced so that it contacts the second, outlet, passageway at the same time as the oblique wall surface of the carrier member contacts the initial part of the oblique wall of the second, outlet, passageway.

The processing zone maybe located substantially in the first passageway or partly in both the first passageway and the second, outlet, passageway providing the first and second, outlet, passageways are continuous with each other.

In one embodiment the mechanism is provided with a third passageway which is continuous with the second, outlet, passageway and orientated in the same plane at a convergent angle of between 45° to 90° to the first passageway, said third passsageway having a width which is sufficient to receive the carrier members to side-to-side contact with each adjacent member.

A further passageway may be provided which is also continuous with the first passageway, said further passageway being a feed passageway having a drive means which acts independently on the or each of the carrier members and a width which is sufficient to receive the or each carrier member in side-to-side contact with an adjacent member, said passageway being orientated at angle of between 45° to 135° to the first passageway.

Thus, the second, outlet, passageway may be at an angle of not greater than 60° to the first passage, for example, 30° or 45° angles and a third passageway may be at an angle of 90° to the first passageway so that the carrier members are taken through an overall change of direction in stages.

According to the present invention there is also provided a carrier member comprising a substantially rectangular body with a lower surface and an upper surface, said upper surface having a plurality of recesses arranged as one or more rows along the longitudinal axis of the carrier member which are adapted to releasably hold receptacles, at least one end of the carrier member terminating in a tapered section with an oblique wall surface angled at less than 90° to the axis and a gear rack extending along one side of the carrier member characterised in that the lower surface of the carrier member has an open-ended inlet groove which forms a passageway from the tapered end and runs parallel with the axis to one or more open-ended outlet grooves each of which leads from the inlet groove at an angle which is the same as that which the oblique wall surface makes with the axis of the carrier member.

The carrier member may have one or both ends which terminate in a tapered section. In the case where both ends terminate in a tapered section each end has an oblique wall on the same side of the carrier member which is at the same angle to the other wall but with an opposite orientation. The open ended inlet groove may lead into two open-ended outlet grooves. Each open ended outlet groove suitably makes an angle of not greater than 60° to the axis of the carrier member.

The carrier members may be composed of any convenient natural or synthetic, hard material. Particularly satisfactory materials are hard, inert materials which have a coefficient of friction of less than 0.75 at an angle of repose in degrees of between 33.0 to 35.0 Synthetic polymeric materials such as natural or synthetic resins or polyethylene, polypropylene, polybutylene, polytetrafluoroethylene are particularly satisfactory. Also, metals, such as stainless steel and natural materials, such as, wood are satisfactory. Preferably the materials should be capable of being moulded and/or easily machined to the desired shape. The materials need to be resistant, as does the material comprising the receptacles, to the substances being used in the processing zone. Thus, if the substances are being analysed or examined in the processing zone the receptacles should be resistant to reagents used or added to the substances. Polytetrafluoroethylene is particularly convenient for it is easily moulded and machined, is hard and inert and has a low coefficient of friction. Each carrier member has steps or a gear rack located along its longitudinal axis for engaging the drive means and for driving each member in succession along a part of the first passageway. The number of steps of the gear rack in one embodiment on each carrier member may be equal in number to the number of receptacles held by the recesses in the carrier member. The carrier members may thus move in an incremental manner through the processing zone.

The aforesaid pivot or pivots project from the floor of the first passageway so that they slidably engage the side walls of the appropriate grooves in the base of the carrier member. The pivots are conveniently steel pin members which may have a head for engaging a recess in the open ended inlet and outlet grooves to rigidly hold the carrier members in position whilst the carrier members move in the horizontal direction.

Figure 2:
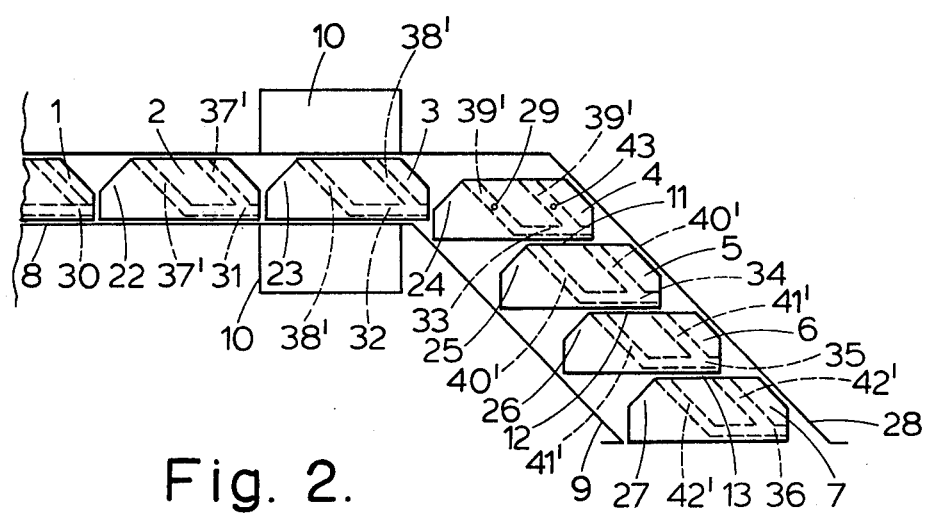
Figure 5:
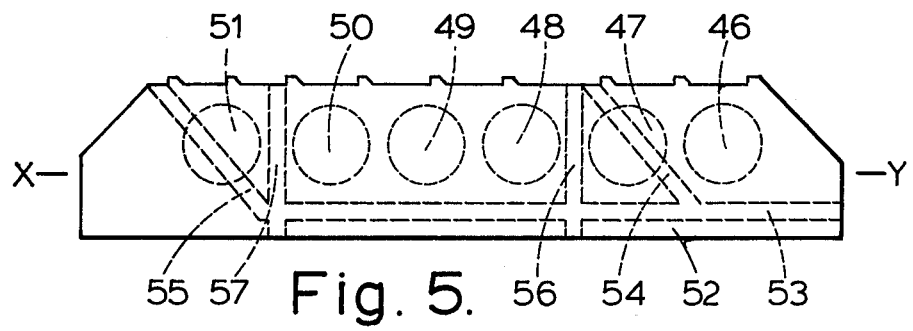
Figure 6:
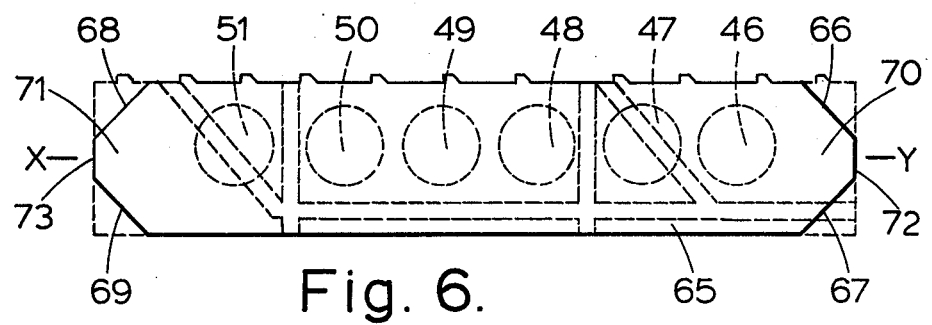
Figure 7:
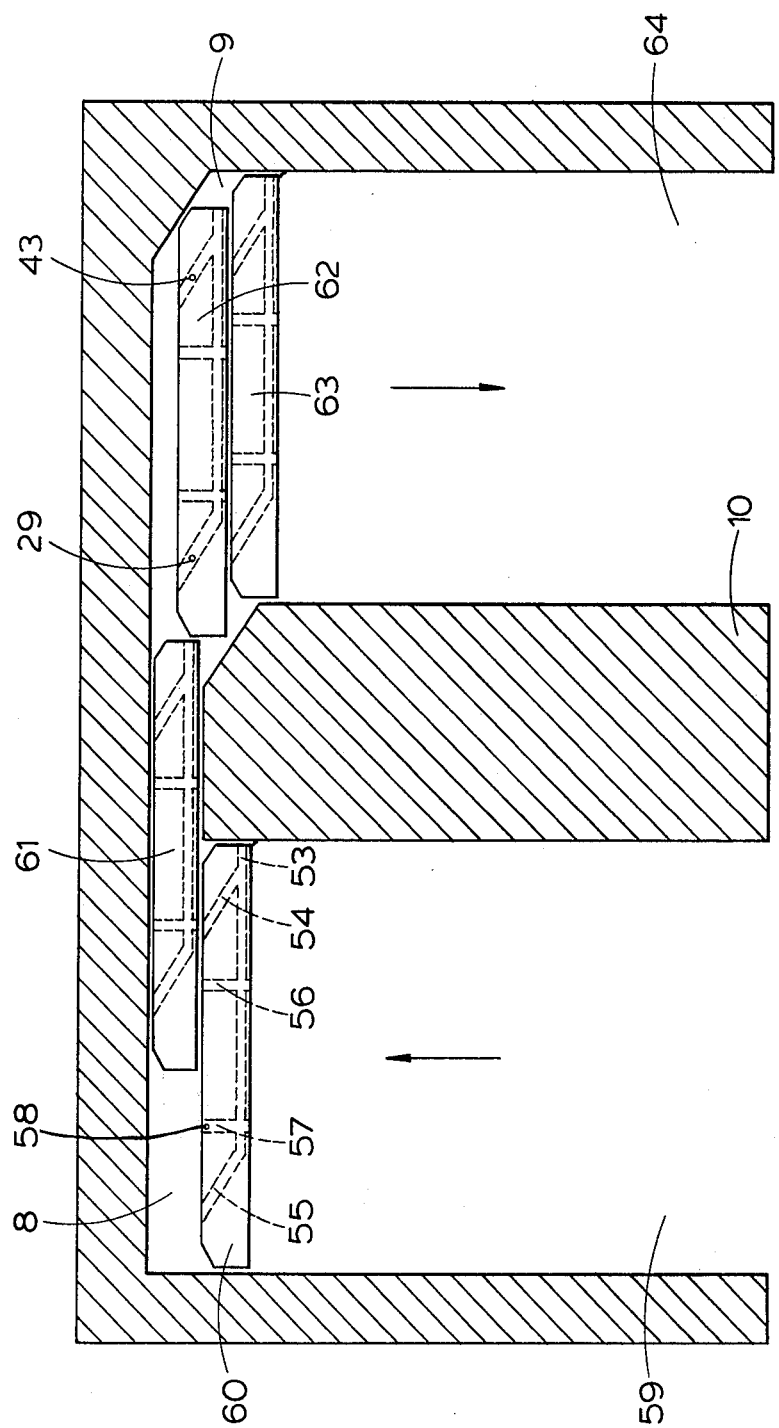

A number of embodiments of the invention will now be described by way of example with reference to FIGS. 1 to 7 of the accompanying drawings, in which:

FIG. 1 is a diagrammatic view in plan of an embodiment of the invention showing the automatic transport mechanism for transporting a series of carrier members through a processing zone, FIG. 2 is a diagrammatic view in plan of an alternative embodiment of an automatic transport mechanism of the invention, FIGS. 3 to 6 are diagrammatic views in plan of carrier members according to the invention, and FIG. 7 is a diagrammatic view in plan of an alternative embodiment of the automatic transport mechanism according to the invention.

FIGS. 1 and 2 respectively illustrate the automatic transport mechanism in which a series of substantially rectangular carrier members 1, 2, 3, 4, 5, 6 and 7 are shown in a first passageway 8 and a second passageway 9. The carrier members are sequentially passed along the first passageway 8 to, and through, a processing zone 10 to the second passageway 9 by a primary driving means (not shown) which acts on a gear rack (see FIGS. 5 and 6) along the length of each carrier member. The primary driving means drives each carrier member in turn, along at least a part of the first passageway 8 after which the carrier members are driven in end-to-end contact by the force from the driving means acting on the rear or trailing end of each carrier member whilst in the first passageway 8 or acting on the rear or trailing side of each carrier member whilst in side-to-side contact in the second passageway 9 for example, by acting on the part sides 11, 12 and 13 of the carrier members 5, 6 and 7. The floors of the two passageways 8, 9 are continuous with each other so that the carrier members may pass freely through the processing zone 10. The processing zone may be incorporated into the first passageway 8 or in a part of the first passageway 8 and a part of the second passageway 9 in order for the process operating in the processing zone to be carried out.

An angle of 45° degrees is made by the second passageway 9 to the first passageway 8 but other angles such as 15 degrees, 30 degrees or 60 degrees to the first passageway are equally satisfactory.

The carrier members 1, 2, 3, 4, 5, 6 and 7 (FIGS. 1 and 2) each have an oblique wall surfaces 15, 16, 17, 18, 19, 20 and 21 which forms a tapered section at the leading end of the carrier members when in the first passageway 8. A similarly angled oblique wall surface 22, 23, 24, 25, 26 and 27 (shown for carrier members 2 to 7 only) forms a tapered section at the trailing end of each carrier member. The oblique wall surfaces respectively of the leading end and the trailing end of each carrier member are on the same side and the carrier members are positioned in the first passageway 8 so that in operation the oblique surface of each leading end slidably engages an oblique wall surface 28 of the second passageway 9. The floor of the first passageway 8 has a metal pin 29 (FIG. 1) which projects in an upward direction to a sufficient distance so that it can enter an open-ended inlet groove 30, 31, 32, 33, 34, 35 and 36 of each respective carrier member 1, 2, 3, 4, 5, 6 and 7 as they pass along the first passageway 8. The inlet grooves are parallel to the longitudinal axis of each carrier member and are continuous with a respective outlet groove 37, 38, 39, 40, 41 and 42 shown for carrier members 2 to 7 only. FIG. 2 illustrates a further outlet groove 37', 38', 39', 40', 41' and 42' continuous with the respective inlet grooves for engaging another pin 43 in the first passageway 8.

Figure 3:
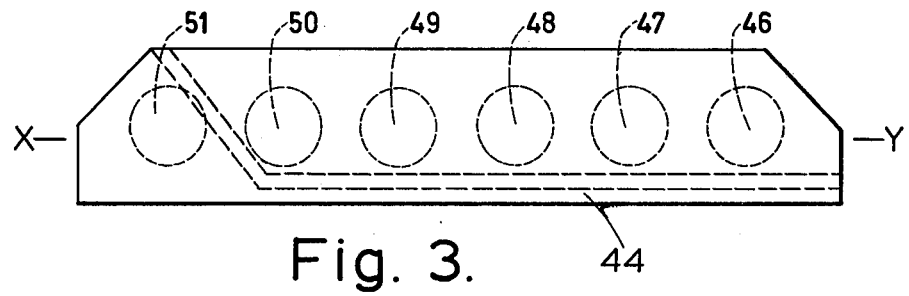
Figure 4:
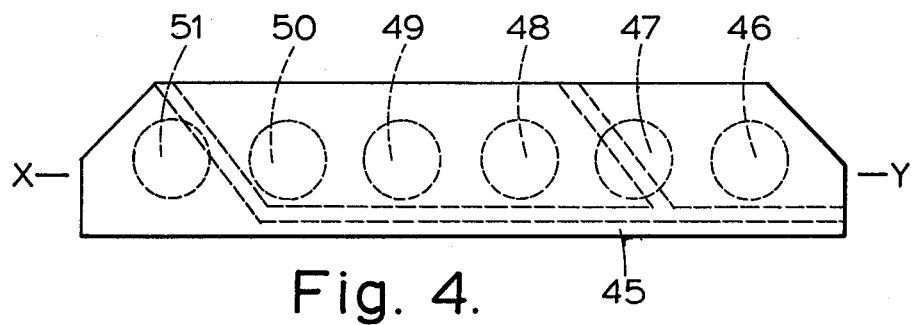

FIG. 3 and FIG. 4 illustrate in more detail two carrier members 44 and 45 respectively which are suitable for use in the automatic transport mechanism of FIG. 1. In the case where two pins 29 and 43 are used (FIG. 2) only the carrier member FIG. 4 with a corresponding number of outlet grooves is suitable. The carrier members shown in plan view FIGS. 3 to 6 have a plurality of recesses 46, 47, 48, 49, 50 and 51 arranged along longitudinal axes X-Y. The recesses of each carrier member are in an upper part of the carrier member whilst the inlet and outlet grooves extend upwards from the floor of a lower part. Thus, receptacles may be releasably held in the recesses of each carrier member and carried to and through the processing zone 10. The receptacles may contain liquids, solid or powders for sampling or analysing on passing through the processing zone. Materials in the processing zone may be freely added or removed from the receptacles whilst in the processing zone 10. If necessary the receptacles may be removed from the carrier members together with the materials contained therein for processing elsewhere. The carrier members alternatively may therefore carry processed materials such as, spools or tapes in a continuous manner for processing.

FIG. 5 illustrates a carrier member 52 in which an open-ended inlet groove 53 has two open-ended outlet grooves 54 and 55 for engaging respective pins in the first passageway 8 and two further open-ended guide grooves 56 and 57 for guiding the carrier member into position when entering the first passageway 9 at right angles as shown in FIG. 7. A guide pin 58 (FIG. 7) in an entry passageway 59 guides carrier member 60 to the first passageway 8. The guide pin 58 passes from the groove 57 as the carrier member 60 enters the first passageway 8 when the proceeding carrier members 61, 62 and 63 are moved towards the second passageway 9. The second passageway 9 is angled at 45° to the first passageway and a third passageway 64 which is continuous with the second passageway 9 and orientated in the same plane is angled at a convergent angle of 45° to the second passageway 9.

FIG. 6 represents a carrier member 65 with a plurality of recesses 46, 47, 48, 49, 50 and 51 arranged along a longitudinal axis X-Y but wherein the leading end (when in use) of the carrier member has two oblique wall surfaces 66, 67 which form a tapered section 70 and the trailing end has two oblique wall surfaces 68, 69 which form a further tapered section 71. The two tapered sections 70, 71 each terminate in a flat portion 72, 73 on the X-Y axis. In operation when the carrier members are in end-to-end contact the flat portions 72, 73 contact corresponding sections on adjacent carrier members. By the use of flat end portions 72, 73 the carrier members are pushed strongly via their ends without tilting and over a part of the second passageway 9 prior to contacting of the trailing end oblique wall surface 69 of the preceeding carrier member. The oblique wall surfaces 66, 68 of the leading edge and the trailing edge respectively on one side of the carrier member 65 may extend across the whole corner if desired. Also the oblique wall surfaces may extend vertically over the full height of the carrier member or only a part of the height thereof if desired, providing the oblique wall surface still acts in a camming fashion on the appropriate oblique wall surface 28 of the second passageway 9. At least a part of the oblique surface or surfaces of the or each carrier member may contain means for actuating the examination, or the processing, of the samples in the receptacles of the carrier member whilst passing through the processing zone. It is understood that any conventional means may be used for actuating the examination, or process, carried out in the processing zone.

We claim:

1. An automatic transport mechanism for transporting a series of carrier members through a processing zone comprising a first passageway along the floor of which substantially rectangular carrier members pass in end to end contact via the processing zone, to a second, outlet, passageway continuous with the first passageway, said second, outlet, passageway being orientated in the same plane at an angle of less than 90° to the first passageway in the direction of passage of the carrier members and having an inner and an outer wall spaced apart with a width which is wider than the first passageway by an amount which is sufficient to allow each carrier member to proceed in side to side contact with adjacent members, means for redirecting each carrier member in turn on passing from the first passageway to the second, outlet, passageway comprising at least one oblique wall surface which forms a tapered section substantially at the leading end of each carrier member for slidably engaging, when in operation, an oblique wall surface formed by at least an initial part of the outer wall of the second, outlet, passageway and characterised in that the floor of the first passageway has at least one pivot which can freely project into an open-ended inlet groove along the base of the carrier member and can be allowed to pass along the groove parallel with the longitudinal axis of the carrier member, after which passage, the or each pivot enters, into slidable engagement with a corresponding number of open-ended outlet grooves continuous with the inlet groove but each orientated at the same angle to the inlet groove as the second, outlet, passageway is orientated to the first passageway, the or each pivot being spaced so that it contacts the second, outlet passageway at the same time as the oblique wall surface of the carrier member contacts the initial part of the oblique wall of the second outlet, passageway.

2. An automatic transport mechanism according to claim 1 in which a third passageway is provided which is continuous with the second, outlet, passageway and orientated in the same plane at a convergent angle of from 45° to 90° to the first passageway, said third passageway having a width which is sufficient to receive the carrier members each in side-to-side contact with the adjacent member.

3. An automatic transport mechanism according to claim 1, in which a feed passageway is provided which is continuous with the first passageway, said feed passageway having a width which is sufficient to receive the or each carrier member in side-to-side contact with an adjacent member, said feed passageway being orientated at an angle of from 45° to 135° to the first passageway.

4. An automatic transport mechanism according to claim 1, in which the second passageway is at an angle of 45° to the first passageway.

5. An automatic transport mechanism according to claim 1, in which the third passageway is at an angle of 90° to the first passageway.

6. An automatic transport mechanism according to claim 1, in which the carrier member has a further series of open-ended inlet grooves which transverse the first open-ended inlet groove at a 90° angle so that the carrier member can engage additional pivots if required.

7. An automatic transport mechanism according to claim 1, in which the carrier member has two open-ended outlet grooves which respectively slidably engage with two pivots in the floor of the first passageway.

8. An automatic transport mechanism according to claim 1, in which both ends of the carrier member terminate with a tapered section with each oblique wall surface being on the same side of the carrier member, one being substantially at the leading end of the carrier member when in motion and the other being substantially at the trailing end, said oblique wall surfaces forming the same angle to the longitudinal axis but in opposite directions and slidably engaging with the respective wall surface of an adjacent carrier member.

9. A carrier member comprising a substantially rectangular body with a lower surface and an upper surface, said upper surface having a plurality of recesses arranged as one or more rows along the longituidnal axis of the carrier member which are adapted to releasably hold receptacles, at least one end of the carrier member terminating in a tapered section with an oblique wall surface angled at less than 90° to the axis and the carrier member characterised in that the lower surface of the carrier member has an open-ended inlet groove which forms a passageway from the tapered end and runs parallel with the axis to one or more open-ended outlet grooves each of which leads from the inlet groove at an angle which is the same as that which the oblique wall surface makes with the axis of the carrier member.

10. A carrier member according to claim 9, in which both ends terminate in a tapered section each end having an oblique wall on the same side of the carrier member which is at the same angle to the other wall but with an opposite orientation.

11. A carrier member according to claim 9, in which the open ended inlet groove leads into two open-ended outlet grooves.

* * * * *